United States Patent [19]

Rohr, Jr.

[11] Patent Number: 4,566,448
[45] Date of Patent: Jan. 28, 1986

[54] LIGAMENT TENSOR AND DISTAL FEMORAL RESECTOR GUIDE

[76] Inventor: William L. Rohr, Jr., 1521 Kimberly Woods, El Cajon, Calif. 92020

[21] Appl. No.: 473,066

[22] Filed: Mar. 7, 1983

[51] Int. Cl.[4] .............................................. A61F 5/04
[52] U.S. Cl. ................................ 128/92 H; 128/92 R
[58] Field of Search ................ 128/303 R, 92 E, 92 H

[56] References Cited

U.S. PATENT DOCUMENTS

| | | | |
|---|---|---|---|
| 4,220,146 | 9/1980 | Cloutier | 128/92 E |
| 4,349,018 | 9/1982 | Chambers | 128/303 R |
| 4,421,112 | 12/1983 | Mains et al. | 128/92 E |
| 4,457,307 | 7/1984 | Stillwell | 128/92 E |
| 4,467,801 | 8/1984 | Whiteside | 128/92 E |

OTHER PUBLICATIONS

Zimmer, Warsaw, In., Publication 81-038-85-04-1025/5M, 1981, "A Manual For Total Knee Replacement Arthroplasty", Nas Eftekhar.
Zimmer, Warsaw, In., Publication 83-038-85-04-0175/10MB, 1982.
Zimmer, "Cloutier TM Total Knee", 1979, B-274 5M679.
Zimmer, "Cloutier TM II Non-Constrained Total Knee System", 1981, 81-038-5701-0968/5MZ.

Primary Examiner—Gene Mancene
Assistant Examiner—C. W. Shedd
Attorney, Agent, or Firm—Sherman & Shalloway

[57] ABSTRACT

A ligament tensor and distal femoral resector guide includes an adjustable support member for mounting on a tibial cutting guide including a guide slot in which is reciprocably mounted a slide member having an arm extending outward therefrom for engaging the condylar notch between the femoral condyles and a screw member threadably engaging the slide member for adjusting the position of the slide member and arm relative to the tibia cutting guide head for establishing tension in the ligaments of a knee structure. A flat pressure plate is removably mounted in the slots of the tibia cutting guide head for engaging the sectioned tibia plateau for applying pressure to the tibia for tensioning of the ligaments. A cutting guide head for guiding the resection of distal femoral condyles is mounted on the adjustable support member.

9 Claims, 4 Drawing Figures

Ligament Tensor and Distal Femoral Resector Guide

BACKGROUND OF THE INVENTION

The present invention relates to orthopedic surgical instruments and pertains particularly to a combination tensor and distal femoral resector guide for utilization in total knee surgical techniques.

During total knee surgery, it is necessary to establish proper alignment of the knee structure and proper tension in the ligaments during the alignment portion of the surgical procedure. Proper tension and alignment at this point in the procedure assures proper fit of the prosthesis and proper tensioning of the ligaments which is necessary for proper functioning of the knee structure after surgery.

The present invention was developed for utilization in conjunction with instrumentation disclosed and claimed in a pending application entitled "Surgical Knee Alignment Method and System", Ser. No. 337,587 filed Jan. 7, 1982 by Thomas D. Petersen. Such instrumentation was developed for achieving superior results from total knee surgery.

The present invention was devised to provide proper tensioning in the ligaments of the knee structure and proper alignment at certain points in the surgical procedures.

SUMMARY AND OBJECTS OF THE INVENTION

It is the primary object of the present invention to provide an improved ligament tensor.

In accordance with the primary aspect of the present invention, a ligament tensor includes stationary support structure including first means for engaging and securing to a tibia with second means for movably mounting on the first support member and including movable means for extending between and engaging the intercondylar notch of a femur for applying pressure thereto and including means for moving the second member relative to the stationary support member for applying a selected tension to the ligaments of a knee structure.

A second aspect of the present invention includes a cutting guide head movable with respect to the support member and independently of the tensor member for selectively positioning cutting guide slots for sectioning of the distal femoral condyles.

BRIEF DESCRIPTION OF THE DRAWINGS

The above and other objects and advantages of the present invention will become apparent from the following description when read in conjunction with the drawings wherein.

DETAILED DESCRIPTION OF A PREFERRED EMBODIMENT

Figure 1:
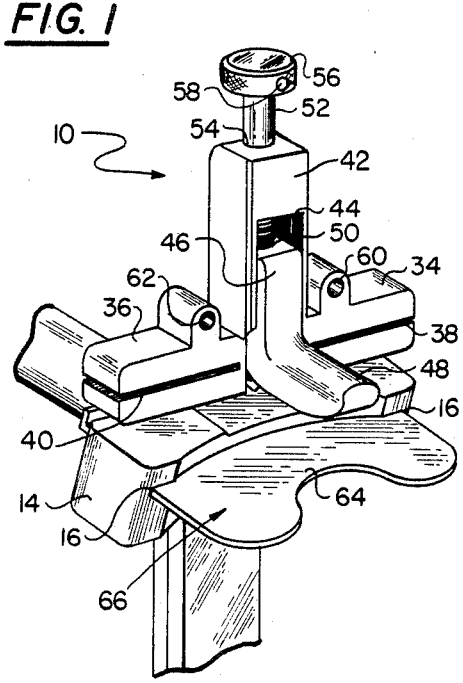
FIG. 1 is a perspective view of a tensor and resector guide in accordance with the invention.
Figure 3:
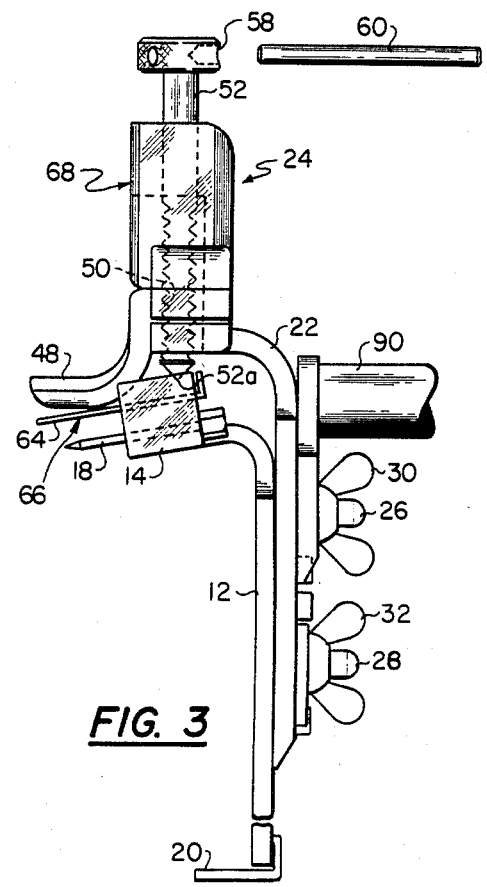
FIG. 3 is a side elevation view of the embodiment of FIG. 1 with the tensor in the retracted position.
Figure 2:
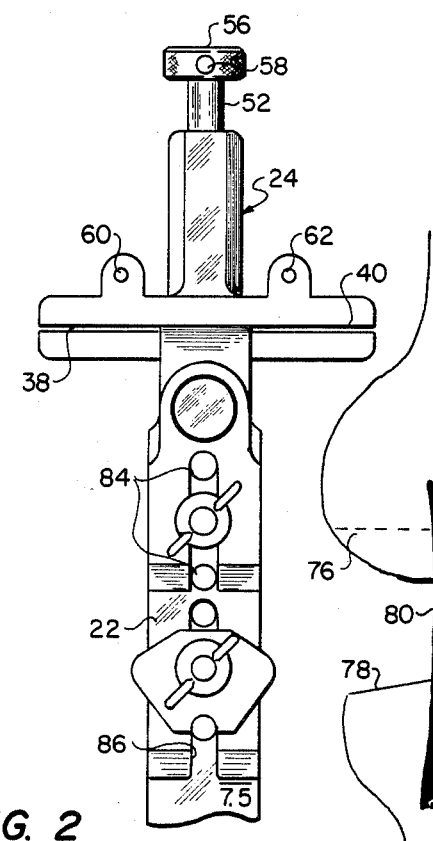
FIG. 2 is a rear elevation view of the embodiment of FIG. 1.

Turning to the drawings, a combination tensor and resector guide in accordance with the invention is illustrated in use in conjunction with a tibia section guide which is utilized as the base support structure. A tibia cutting guide includes an elongated shank or bar member 12 having a curved upper end which supports a tibia cutting guide head 14. The cutting guide head is positioned and angled to guide the cutting or resectioning of a tibial plateau for total knee surgery. The cutting guide head 14 includes a transverse cutting guide slot 16. A pair of anchoring pins 18 extend through a pair of spaced apart bores in the cutting guide head 14 for anchoring it to the upper end of a tibia. An ankle guide bracket 20 attached to the lower end of the shank or bar 12 engages the tibia at the ankle for supporting and aligning the tibia cutting guide structure.

The present invention comprises an attachment for attaching to and supporting on the tibia cutting guide and for applying the proper selected tension to the ligaments of the knee structure during appropriate stages of the surgical procedures. The present invention comprises a frame in the form of a generally elongated flat bar member 22 that has a curved upper end which supports a support housing structure 24 to be more specifically described. The support member 22 includes a plurality of bores 84 and an elongated slot 86 for fitting over and adjusting relative to a pair of bolts or studs 26 and 28 supported on the support member 12 and including thumb screws or nuts 30 and 32 for securing the members in position relative to each other.

The support housing structure 24 has a generally T-shaped configuration with a pair of outwardly extending arms 34 and 36 having cutting guide slots 38 and 40 formed therein for guiding the cutting of the femoral condyles. A central upwardly extending support member 42 includes a guide slot 44 in which is mounted a slide member 46 having an outwardly extending arm 48 thereon. The slide member 46 is reciprocably mounted within the slide or guide slot 44 and includes a central threaded bore 50 which is threadably engaged by a threaded screw or shaft 52 which is rotatably mounted within a nonthreaded bore 54 in the vertical support member 42. A head 56 on the upper end of the screw member 52 includes a plurality of radially extending bores 58 for receiving a torque handle 60 for applying torque to the screw. The screw 52 includes a lower end or tip 52a in the form of a pointed or generally conical bearing structure that engages the upper surface of the tibia cutting guide head 14 and is supported axially thereby for raising the slide member 46 upon rotation thereof.

The arm 48 extends into the intercondylar notch between the pair of condyles at the end of the femur (FIG. 4) when the leg is in extension for engaging and applying thereto a force for tensioning the ligaments. A pair of laterally spaced bores 60 and 62 are formed in the arm members 34 and 36 and receive a pair of anchoring pins 64 for anchoring the condylar resector guide to the femur.

The central support structure or member 42 is provided with a flat, straight or planar surface 68, which is adapted to lie flat against a preplaned or filed flat surface 82 on the anterior femoral cortex. This surface 82 is prepared to lie parallel to the axis of the femur. The surface 68 extends parallel to the axis of the tibia where the guide assembly 12 is properly mounted on the tibia. Consequently, when the surfaces 68 and 82 align with each other, the leg is held in absolute 180° of extension.

Figure 4:
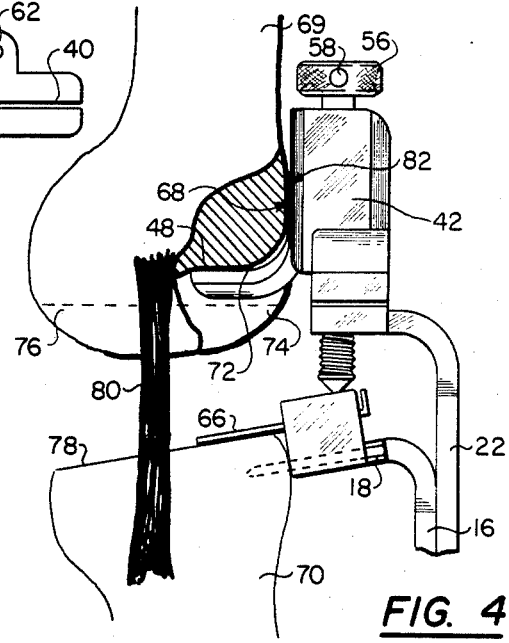
FIG. 4 is a view like FIG. 3 showing the tensor in the extended position.

Referring to FIG. 4, the instrument is shown installed in a knee joint structure between a femur 69 and a tibia 70. The arm 48 is shown engaging a notch surface 72 between condyles 74 and 76 on femur 69. The pressure plate 66 mounted in slot 16 of the tibia cutting guide head 14 engages the sectioned surface 78 of the tibia 70. Extension of the screw 52 spreads the arm 48 and plate 66 apart applying tension to the ligaments 80 (only one of which is shown).

In use, the pressure plate 66 is inserted in the guide slot 16 of the properly mounted tibia cutting guide head 14 and rests on top of the sectioned surface 78 of the tibia 70 as shown in FIG. 4. The arm 48 extends outward and into engagement with the surface 72 in the condylar slot between the condyles 74 and 76 as shown in FIG. 4. Rotation of the threaded shank or screw 52 raises the slide 46 and attached arm 48 upward for engagement with the notch surface 72 between the condyles 74 and 76 and for beginning to apply a tension to the ligaments 80. Movement of the arm 48 upward, as shown in FIG. 4 with the knee extended to the 180° position (i.e. surfaces 68 and 82 aligned), applies a tension to the ligaments 80 of the knee structure. A selected desired amount of tension may be applied to the ligaments. As soon as the proper tension is established, the nut 30 may be loosened and the handle 90 may be removed from its mounting on stud 26. The cutting slots 38 and 40 are selectively positioned according to prior indication by another instrument for the desired position of cut of the condyles 74 and 76. As soon as the desired cut is provisionally selected, a provisional mark may be made on the condyle, and the knee may then be flexed to thereby disengage the arm 48 from the condylar notch to view the preselected or established marks on the condyles to ascertain the desired depth of cut. The knee may then be moved back to the extended position of 180° of flexion with the ligaments properly tensioned without disturbing the setting of the tensor (screw 52).

The bores 84 in support member 22 are positioned and spaced according to predetermined spacing required between slots 16 of the tibia guide 14 and slots 38 and 40 of the femoral cutting guide. These spacings are predetermined by the indicated size of prosthesis for the knee.

Because the tensioning device is centrally located, (i.e. arm 48 engages center of knee structure) medial and deviation adjustments in the fitting of the knee prosthesis are possible. The tensioning device does not interfere with the process of aligning the load bearing axis of the led during the performance of the operation.

While I have illustrated and described my invention by means of specific embodiments, it is to be understood that numerous changes and modifications may be made therein without departing from the spirit and scope of the invention as defined in the appended claims.

I claim:

1. A ligament tensor for tensioning the ligaments in a knee structure during knee surgery, comprising:
   a support frame,
   first mounting means for mounting said support frame to a tibia;
   second means for noninvasively engaging a distal end of a femur and
   means interacting between said first mounting means and second means for moving said second means relative to said first mounting means for tensioning the ligaments in said knee structure, said means interacting comprising:
   (a) a threaded hole extending through said second means;
   (b) a threaded screw threadably extending through said threaded hole and engagable with said first mounting means;
   (c) said second means being constrained from rotation about an axis defined by said threaded hole whereby rotation of said threaded screw with respect to said threaded hole in a first direction tensions said ligaments while rotation of said threaded screw with respect to said threaded hole in a second direction contracts said ligaments.

2. The ligament tensor of claim 1 wherein:
   said support frame includes a condyle cutting guide for guiding the cutting of the distal femoral condyles.

3. The ligament tensor of claim 2 wherein said second means comprises
   a slide member, and
   an arm carried by said slide member.

4. The ligament tensor of claim 3 wherein said first mounting means comprises a tibia cutting guide assembly including an elongated frame member for alignment with the tibia and a cutting guide head for securing adjacent the tibia plateau and a plate mounted in said cutting guide head for engaging a preselected planar surface of the tibia.

5. The ligament tensor of claim 4 wherein said support frame includes an elongated bar slidably mounted on said tibia cutting guide frame, and
   said arm is movable within said guide independently of said support frame.

6. The ligament tensor of claim 5 wherein said support frame includes an elongated member having a planar alignment surface for engaging a prepared flat surface on a femoral condyle for indicating true leg alignment.

7. The ligament tensor of claim 6 where said screw is axially supported on said tibia cutting guide head.

8. The ligament tensor of claim 7 wherein said condyle cutting guide comprises a pair of opposed arms extending outward in opposite directions from said elongated member and including guide slots therein for cutting the distal femoral condyles.

9. The ligament tensor of claim 8 wherein said elongated member includes an elongated rectangular slot and said slide member is slidably mounted in said slot to thereby constrain rotation of said slide member with respect to said elongated member.

* * * * *